United States Patent
Bek et al.

(10) Patent No.: US 9,155,583 B2
(45) Date of Patent: *Oct. 13, 2015

(54) SYSTEMS AND METHODS FOR MONITORING AND CONTROLLING USE OF MEDICAL DEVICES

(75) Inventors: Robin Bek, Campbell, CA (US); Jay Qin, Fremont, CA (US); John Gaiser, Mountain View, CA (US); David S. Utley, Redwood City, CA (US); James J. Bernitt, Yorktown Heights, NY (US)

(73) Assignee: Mederi Therapeutics, Inc., Norwalk, CT (US)

( * ) Notice: Subject to any disclaimer, the term of this patent is extended or adjusted under 35 U.S.C. 154(b) by 932 days.

This patent is subject to a terminal disclaimer.

(21) Appl. No.: 12/927,353

(22) Filed: Nov. 12, 2010

(65) Prior Publication Data

US 2011/0098698 A1  Apr. 28, 2011

Related U.S. Application Data

(60) Division of application No. 11/638,958, filed on Dec. 14, 2006, now abandoned, which is a division of application No. 10/792,423, filed on Mar. 3, 2004, now abandoned, which is a division of application No. 10/070,465, filed as application No. PCT/US00/40881 on Sep. 7, 2000, now Pat. No. 6,733,495, and a continuation-in-part of application No. 09/639,910, filed on Aug. 16, 2000, now abandoned, and a continuation-in-part of application No. 09/574,704, filed on May 18, 2000, now Pat. No. 6,464,689, which is a continuation-in-part of application No. 09/495,390, filed on Jan. 31, 2000, now abandoned.

(51) Int. Cl.
*A61B 18/14* (2006.01)
*A61B 18/00* (2006.01)
*A61B 19/00* (2006.01)
*A61B 17/00* (2006.01)

(52) U.S. Cl.
CPC ............. *A61B 18/00* (2013.01); *A61B 18/1477* (2013.01); *A61B 19/44* (2013.01); *A61B 18/1492* (2013.01); *A61B 2017/00017* (2013.01); *A61B 2017/00084* (2013.01); *A61B 2017/00199* (2013.01); *A61B 2017/00269* (2013.01); *A61B 2017/00482* (2013.01); *A61B 2018/0022* (2013.01); *A61B 2018/00267* (2013.01); *A61B 2018/00494* (2013.01); *A61B 2018/00988* (2013.01); *A61B 2019/4873* (2013.01)

(58) Field of Classification Search
USPC ...................... 606/1, 32–34, 41; 607/101–102
See application file for complete search history.

(56) References Cited

U.S. PATENT DOCUMENTS

| | | |
|---|---|---|
| 1,798,902 A | 3/1931 | Raney |
| 3,517,128 A | 6/1970 | Hines |

(Continued)

FOREIGN PATENT DOCUMENTS

| | | |
|---|---|---|
| DE | 4 303 882 | 2/1995 |
| DE | 3 838 840 | 2/1997 |

(Continued)

OTHER PUBLICATIONS

Castell, D. O. Gastrophageal Reflux Disease: Current Strategies for Patient Management: Arch Fam. Med 5(4): 221-7; Apr. 1996.

(Continued)

*Primary Examiner* — Michael Peffley

(57) ABSTRACT

A device carries a use monitoring element that possesses a state or condition that changes in response to use of the device and that is sensed when the device is presented for use. Reuse of the device is not permitted, if the use monitoring element indicates a prior use.

9 Claims, 9 Drawing Sheets

(56) References Cited

U.S. PATENT DOCUMENTS

| | | |
|---|---|---|
| 3,901,241 A | 8/1975 | Allen, Jr. |
| 4,011,872 A | 3/1977 | Komiya |
| 4,196,724 A | 4/1980 | Wirt et al. |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |
| 4,705,041 A | 11/1987 | Kim |
| 4,858,615 A | 8/1989 | Meinema |
| 4,901,737 A | 2/1990 | Toone |
| 4,906,203 A | 3/1990 | Margrave et al. |
| 4,907,589 A | 3/1990 | Cosman |
| 4,943,290 A | 7/1990 | Rexroth et al. |
| 4,947,842 A | 8/1990 | Marchosky et al. |
| 4,955,377 A | 9/1990 | Lennox et al. |
| 4,966,597 A | 10/1990 | Cosman |
| 4,976,711 A | 12/1990 | Parins et al. |
| 5,019,075 A | 5/1991 | Spears et al. |
| 5,035,696 A | 7/1991 | Rydell |
| 5,046,512 A | 9/1991 | Murchie |
| 5,047,028 A | 9/1991 | Qian |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,122,137 A | 6/1992 | Lennox |
| 5,125,928 A | 6/1992 | Parins et al. |
| 5,156,151 A | 10/1992 | Imran |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,232,444 A | 8/1993 | Just et al. |
| 5,233,515 A | 8/1993 | Cosman |
| 5,236,413 A | 8/1993 | Fiering |
| 5,242,441 A | 9/1993 | Avitall |
| 5,254,126 A | 10/1993 | Filipi et al. |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,334,196 A | 8/1994 | Scott et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,347 A | 11/1994 | Nguyen |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,383,874 A | 1/1995 | Jackson et al. |
| 5,383,876 A | 1/1995 | Nardella |
| 5,383,917 A | 1/1995 | Desai et al. |
| 5,385,544 A | 1/1995 | Edwards et al. |
| 5,397,339 A | 3/1995 | Desai |
| 5,398,683 A | 3/1995 | Edwards et al. |
| 5,400,267 A | 3/1995 | Denen et al. |
| 5,401,272 A | 3/1995 | Perkins |
| 5,403,311 A | 4/1995 | Abele et al. |
| 5,409,453 A | 4/1995 | Lundquist et al. |
| 5,409,483 A | 4/1995 | Cambell et al. |
| 5,415,657 A | 5/1995 | Taymor-Luia |
| 5,421,819 A | 6/1995 | Edwards et al. |
| 5,423,808 A | 6/1995 | Edwards et al. |
| 5,423,811 A | 6/1995 | Imran et al. |
| 5,423,812 A | 6/1995 | Ellman et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,411 A | 12/1995 | Montag et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards et al. |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,599,345 A | 2/1997 | Edwards et al. |
| 5,609,151 A | 3/1997 | Mulier et al. |
| 5,624,439 A | 4/1997 | Edwards et al. |
| 5,651,780 A * | 7/1997 | Jackson et al. ............ 606/1 |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,732,698 A | 3/1998 | Swanson et al. |
| 5,738,096 A | 4/1998 | Ben-Haim |
| 5,742,718 A * | 4/1998 | Harman et al. ............ 385/53 |
| 5,743,903 A | 4/1998 | Stern et al. |
| 5,830,213 A | 11/1998 | Panescu et al. |
| 5,836,874 A | 11/1998 | Swanson et al. |
| 5,848,969 A | 12/1998 | Panescu et al. |
| 5,860,974 A | 1/1999 | Abele |
| 5,871,483 A | 2/1999 | Jackson et al. |
| 5,891,030 A | 4/1999 | Johnson et al. |
| 5,916,163 A | 6/1999 | Panescu et al. |
| 5,931,835 A | 8/1999 | Mackey |
| 5,957,961 A | 9/1999 | Maguire et al. |
| 6,004,269 A | 12/1999 | Crowley et al. |

(56) References Cited

U.S. PATENT DOCUMENTS

| | | | |
|---|---|---|---|
| 6,006,755 A | 12/1999 | Edwards | |
| 6,014,581 A | 1/2000 | Whayne et al. | |
| 6,023,638 A | 2/2000 | Swanson | |
| 6,044,846 A | 4/2000 | Edwards et al. | |
| 6,056,744 A | 5/2000 | Edwards | |
| 6,063,082 A | 5/2000 | DeVore et al. | |
| 6,092,528 A | 7/2000 | Edwards et al. | |
| 6,106,460 A | 8/2000 | Panescu et al. | |
| 6,165,169 A | 12/2000 | Panescu et al. | |
| 6,237,604 B1 | 5/2001 | Burnside et al. | |
| 6,254,598 B1 | 7/2001 | Edwards et al. | |
| 6,358,245 B1 | 3/2002 | Edwards et al. | |
| 6,387,092 B1* | 5/2002 | Burnside et al. | 606/32 |
| 6,391,024 B1* | 5/2002 | Sun et al. | 606/34 |
| 6,402,742 B1 | 6/2002 | Blewett et al. | |
| 6,464,689 B1 | 10/2002 | Qin et al. | |
| 6,464,697 B1 | 10/2002 | Edwards et al. | |
| 6,544,226 B1 | 4/2003 | Gaiser et al. | |
| 6,547,776 B1 | 4/2003 | Gaiser et al. | |
| 6,589,238 B2 | 7/2003 | Edwards et al. | |
| 6,645,201 B1 | 11/2003 | Utley et al. | |
| 6,695,806 B2 | 2/2004 | Gelfand et al. | |
| 6,699,243 B2 | 3/2004 | West et al. | |
| 6,733,495 B1 | 5/2004 | Bek et al. | |
| 6,783,523 B2 | 8/2004 | Qin et al. | |
| 6,790,207 B2 | 9/2004 | Utley et al. | |
| 6,802,841 B2 | 10/2004 | Utley et al. | |
| 6,827,713 B2 | 12/2004 | Bek et al. | |
| 6,994,704 B2 | 2/2006 | Qin et al. | |
| 7,922,715 B2 | 4/2011 | Qin et al. | |
| 8,257,346 B2 | 9/2012 | Qin et al. | |
| 2002/0151871 A1 | 10/2002 | Gaiser et al. | |
| 2002/0162555 A1 | 11/2002 | West et al. | |
| 2002/0193787 A1 | 12/2002 | Qin et al. | |
| 2002/0198519 A1 | 12/2002 | Qin et al. | |
| 2004/0089313 A1 | 5/2004 | Utley et al. | |

FOREIGN PATENT DOCUMENTS

| | | |
|---|---|---|
| EP | 0 139 607 | 5/1985 |
| EP | 0 608 609 | 8/1994 |
| EP | 0 765 813 | 4/1997 |
| WO | WO 91/01773 | 2/1991 |
| WO | WO 92/10142 | 6/1992 |
| WO | WO 93/08755 | 5/1993 |
| WO | WO 94/10925 | 5/1994 |
| WO | WO 94/21165 | 9/1994 |
| WO | WO 94/21178 | 9/1994 |
| WO | WO 94/22366 | 10/1994 |
| WO | WO 94/26178 | 11/1994 |
| WO | WO 95/18575 | 7/1995 |
| WO | WO 95/19142 | 7/1995 |
| WO | WO 95/25472 | 9/1995 |
| WO | WO 96/00042 | 1/1996 |
| WO | WO 96/16606 | 6/1996 |
| WO | WO 96/29946 | 10/1996 |
| WO | WO 97/06857 | 2/1997 |
| WO | WO 97/32532 | 9/1997 |
| WO | WO 97/43971 | 11/1997 |
| WO | WO 99/17671 | 4/1999 |

OTHER PUBLICATIONS

Reynolds, "Influence of Pathophysiology, Severity, and Cost on the Med. Management of Gastroesophageal Reflux Disease." Am. J. Health-Syst Pharm. 53(22 suppl 3): S5-12; Nov. 1996.

Dallemagne, B. et al., "Laparoscopic Nissen Fundoplication: Preliminary." Surgical Laparoscopy & Endoscopy. 1991 1(3) 138-43.

Kelly, KA et al., "Duodenal-Gastric Reflux and Slowed Gastric Emptying by Electrical Pacing of the Canine Duodenal Pacesetter Potential." Gastroenterology. 1997.72(3):429-33.

Urschel J. D "Complications of Antireflux Surgery". Am J. Surg. 1993 166(1): 68-70.

Kaneko, et al., Physiological Laryngeal Pacemaker, May 1985, Trans Am Soc. Artif. Intern Organs, vol. XXXI, pp. 293-296.

Karlstrom, L.J. et al., Extopic Jejunal Pacemakers and Enterogastric Reflux after Roux Gastrectomy: Effect of Intestinal Pacing.: Surgery 1989. 106(3): 486-495.

Mugica et al., Neurostimulation: An overview, Chapter 21, Preliminary Test of a Muscular Diaphragm Pacing System on Human Patients. 1985. pp. 263-279.

Rice, et al. Enoscopic Paranasal Sinus Surgery. Chapter 5, Functional Endoscopic Paranasal Sinus Surgery, The Technique of Messerklinger, Raven Press, 1988, pp. 75-104.

Mugica et al. Direct Diaphragm Stimulation, Jan. 1987 PACE, vol. 10, pp. 252-256.

Hinder, R.A et al., "The technique of laparoscopic Nissen Fundoplication." Surgical Laparoscopy & Endoscopy. 1992. 2(3): 265-272.

Rice et al., Endoscopic Paranasal Sinus Sugery. Chapter 6, Functional Endoscopic Paranasal Sinus Surgery, The Technique of Wigand, Raven Press, 1988, pp. 105-125.

* cited by examiner

SYSTEMS AND METHODS FOR MONITORING AND CONTROLLING USE OF MEDICAL DEVICES

RELATED APPLICATIONS

This application is a divisional of U.S. patent application Ser. No. 11/638,958, filed 14 Dec. 2006, now abandoned, which is a divisional of U.S. patent application Ser. No. 10/792,423, filed 3 Mar. 2004, now abandoned, which is a divisional of U.S. patent application Ser. No. 10/070,465, filed Aug. 14, 2002, now U.S. Pat. No. 6,733,495, which is a National Stage Entry of PCT/US00/40881, filed Sep. 9, 2000, which claims the benefit of provisional U.S. Patent Application Ser. No. 60/152,749, filed 8 Sep. 1999, and entitled "Systems and Methods for Monitoring and Controlling Use of Medical Devices," and which is also a continuation-in-part of U.S. application Ser. No. 09/495,390, filed 31 Jan. 2000, and entitled "Systems and Methods for Monitoring and Controlling Use of Medical Devices, now abandoned, and a continuation-in-part of U.S. patent application Ser. No. 09/574,704, filed 18 May 2000, and entitled "Graphical User Interface for Monitoring and Controlling Use of Medical Devices, now U.S. Pat. No. 6,464,689," and a continuation-in-part of U.S. patent application Ser. No. 09/639,910 filed 16 Aug. 2000, and entitled "Unified Systems and Methods for Controlling Use and Operation of a Family of Different Treatment Devices," now abandoned.

FIELD OF THE INVENTION

The invention is directed to systems and methods for monitoring and controlling use of medical devices.

BACKGROUND OF THE INVENTION

Use of medical devices intended to treat or diagnose conditions of the body can sometimes generate stress on the material or materials from which the devices are made. The material stress can alter the physical characteristics of the devices, making future performance of the devices unpredictable.

In addition, exposure to blood and tissue during use can entrap biological components on or within many medical devices. Despite cleaning and subsequent sterilization, the presence of entrapped biological components can lead to unacceptable pyrogenic reactions.

The effects of material stress and damage caused during a single use of a medical device, coupled with the possibility of pyrogen reactions even after resterilization, reasonably justify imposing a single use restriction upon many medical devices.

SUMMARY OF THE INVENTION

The invention provides systems and methods for monitoring and controlling use of a device for treating a tissue region. The systems and methods provide the device and an element carried by the device for retaining use monitoring information. The systems and methods employ a reader to download from the element the use monitoring information to a controller for the device. The systems and methods cause the controller to process the use monitoring information by pre-programmed rules to either enable or disable operation of the device.

According to one aspect of the invention, the element retains use monitoring information as an identification code unique to the device. The pre-programmed rules cause the controller to create a table by registering unlike identification codes in memory as they are downloaded by the reader and to enable operation of the device when a new identification code is registered in the table. The pre-programmed rules cause the controller to disable operation of the device when the given identification code matches an identification code in the table.

The element can express the identification code using, e.g., a magnetic core element, or a bar code strip, or a RFID tag, or by Hall effect, or by an array of fiber optics.

According to another aspect of the invention, the element retains use monitoring information as a value reflecting time period of use of the device. The pre-programmed rules cause the controller to enable operation of the device only when the value reflects a time period of use less than a prescribed maximum time period of use.

The element can express the value using, e.g., a magnetic core element, or a bar code strip, or a RFID tag, or a stepper motor.

According to another aspect of the invention, the element includes a magnetic core carried by the device having a logic state that changes in response to use of the device. In one embodiment, magnetic flux in one direction about the core represents a logic one state and magnetic flux in another direction about the core represents a logic zero state. The core, when initially installed in the device, possesses a logic one state. Use of the device changes the logic state to a logic zero state. When the device is presented for use, the state of the core is sensed. If the core indicates a prior use (logic zero state), reuse of the device is not permitted.

According to another aspect of the invention, the element includes a latching relay carried by the device having a relay condition that changes in response to use of the device. In one embodiment, the relay is biased toward an electrically open condition. The relay can be moved and latched into an electrically closed condition. Prior to use, the relay is located in the electrically open condition. During use, the relay is moved and latched to the electrically closed condition. When the device is presented for use, the position of the relay is sensed. If the position indicates a prior use (latched closed condition), reuse of the device is not permitted.

According to another aspect of the invention, the element includes a use register carried by the device that retains a digital value that changes in response to use of the device. In one embodiment, when the device is presented for use, the value contained in the use register is sensed. If the value indicates a prior use, reuse of the device is not permitted.

Features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

Figure 1:
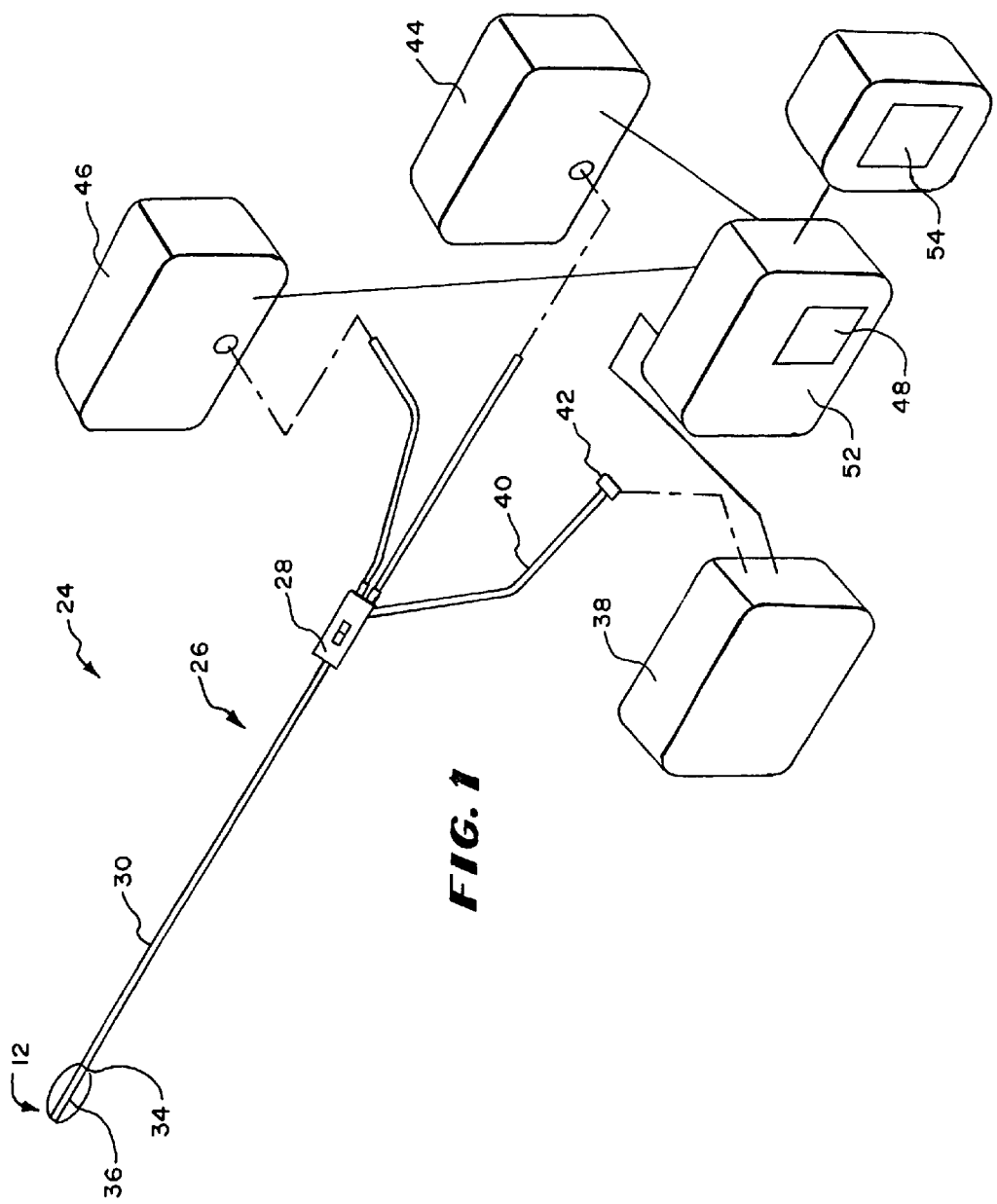
FIG. 1 is a diagrammatic view of a system for treating body sphincters and adjoining tissue regions, which embodies features of the invention.

FIG. 1 shows one embodiment of a system 10, which monitors and controls the use of an operative element 12. The system 10 is well adapted for association with single use, catheter-based devices. Therefore, in the illustrated embodiment, the operative element 12 is part of a catheter-based treatment device 26. It should be appreciated, however, that the system 10 is also adaptable for use with devices and methods that are not necessarily catheter-based.

A. The Treatment Device

In the illustrated embodiment, the device 26 includes a handle 28 made, e.g., from molded plastic. The handle 28 is sized to be conveniently held by a physician, to introduce the catheter tube 30 into the targeted tissue region.

The handle 28 carries a flexible catheter tube 30. The catheter tube 30 can be constructed, for example, using standard flexible, medical grade plastic materials. The catheter tube 30 has a distal end 34, which carries the operative element 12.

The operative element 12 can support, for example, a device for imaging body tissue, such as an endoscope, or an ultrasound transducer. The operative element 12 can also support a device to deliver a drug or therapeutic material to body tissue. The operative element 12 can also support a device for sensing a physiological characteristic in tissue, such as electrical activity, or for transmitting energy to stimulate or form lesions in tissue.

In the illustrated embodiment, the device 26, in use, is intended to treat dysfunction of sphincters and adjoining tissue regions in the upper gastrointestinal tract, e.g., in the lower esophageal sphincter and adjacent cardia of the stomach, as well as in the lower gastrointestinal tract, e.g., in the intestines, rectum and anal canal. Still, it should be appreciated that the system 10 can be used in association with other devices and methods used to treat other dysfunctions elsewhere in the body, which are not necessarily sphincter-related. For example, the various aspects of the invention have application in procedures requiring ablation of tissue throughout the body, or treatment of hemorrhoids, or restoring compliance to or otherwise tightening interior tissue or muscle regions.

In the illustrated embodiment, one function that the operative element 12 is to perform is to apply energy in a selective fashion to a targeted body region, which, for the purpose of illustration, can be the lower esophageal sphincter, or cardia, or both. The applied energy creates one or more lesions, or a prescribed pattern of lesions, below the mucosal surface of the esophagus or cardia. The subsurface lesions are formed in a manner that preserves and protects the mucosal surface against thermal damage.

It has been discovered that natural healing of the subsurface lesions leads to a physical tightening of the sphincter and/or adjoining cardia. The subsurface lesions can also result in the interruption of aberrant electrical pathways that may cause spontaneous sphincter relaxation. In any event, the treatment can restore normal closure function to the sphincter.

Figure 2:
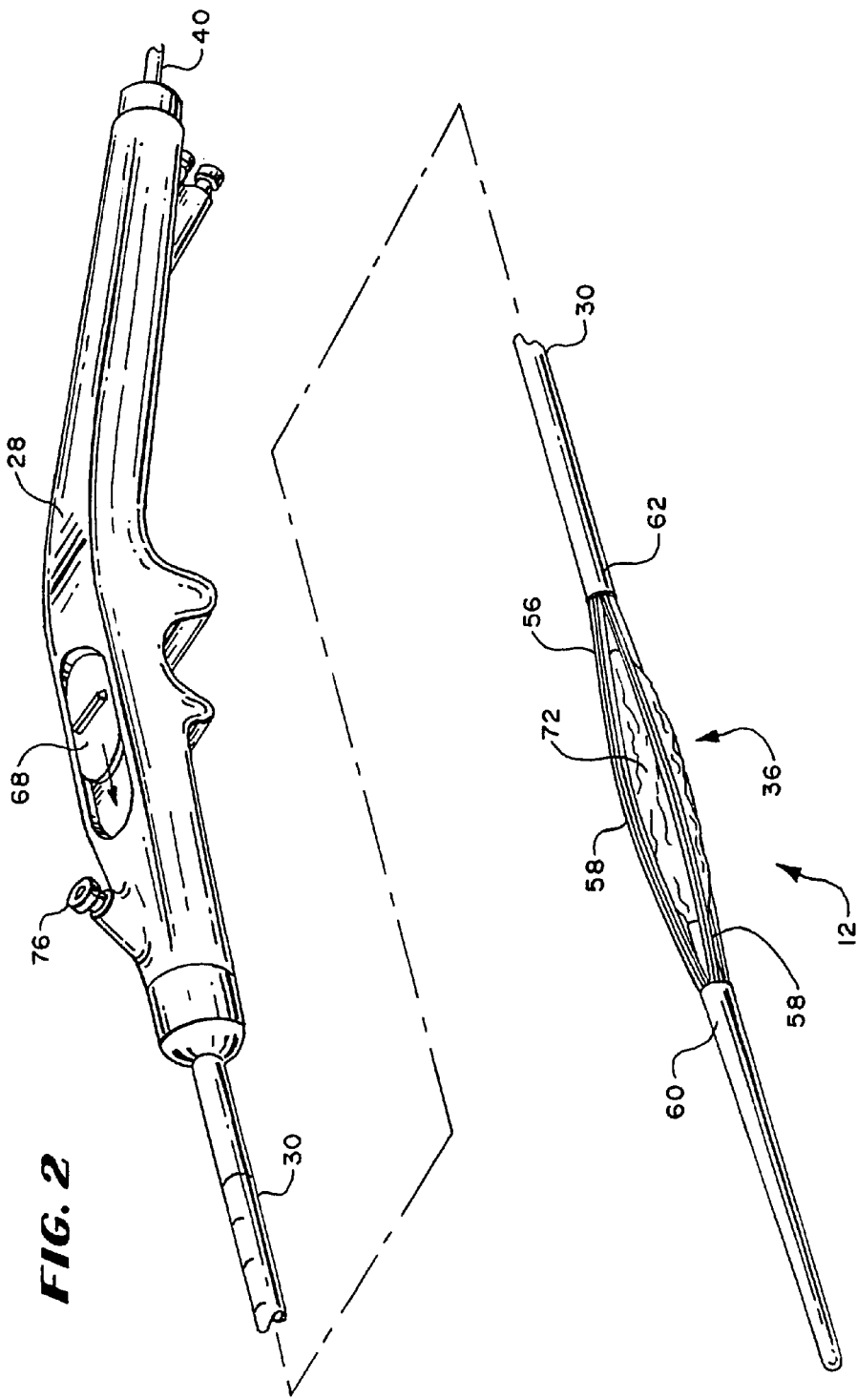
FIG. 2 is a perspective view, with portions broken away, of a device usable in association with the system shown in FIG. 1 having an operative element for contacting tissue shown in a collapsed condition.
Figure 3:
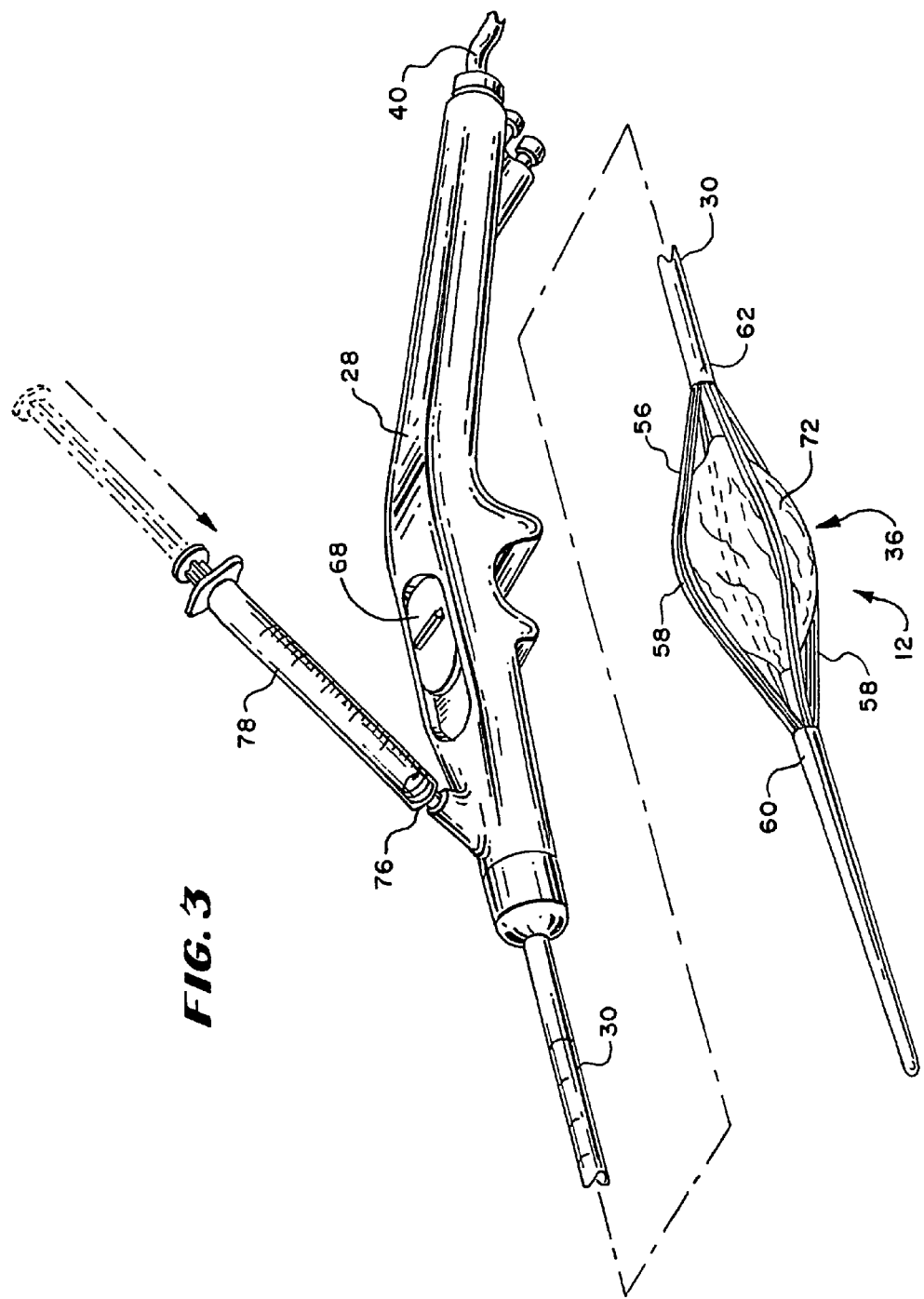
FIG. 3 is a perspective view, with portions broken away, of the device shown in FIG. 2, with the operative element shown in an expanded condition.
Figure 4:
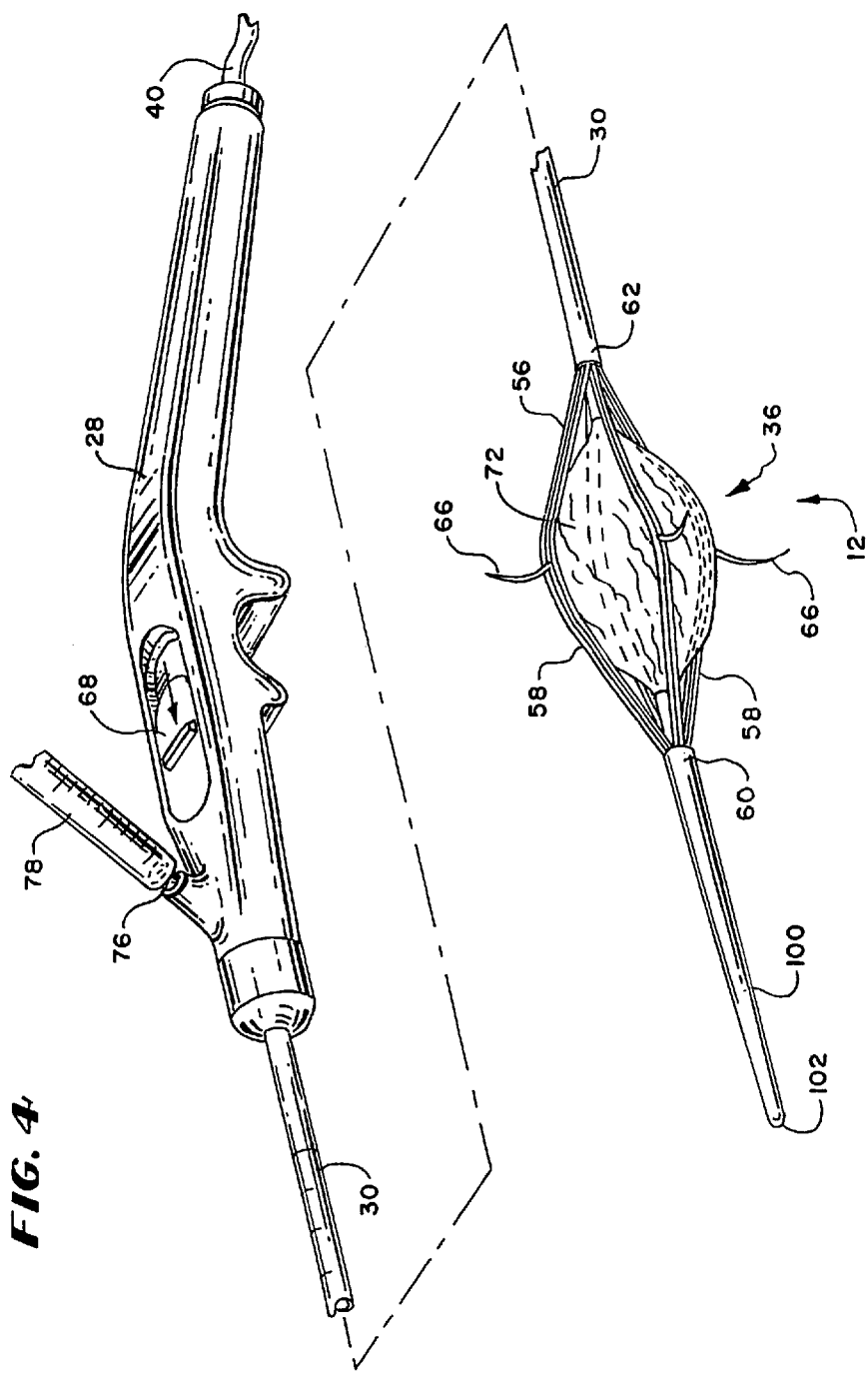
FIG. 4 is a perspective view, with portions broken away, of the device shown in FIG. 2, with the operative element shown in an expanded condition and the electrodes extended for use.

The structure of the operative element 12 to achieve this result can vary. A representative embodiment is shown in FIGS. 2 to 4, in which the operative element 12 comprises a three-dimensional basket 56. The basket 56 includes one or more spines 58, and typically includes from four to eight spines 58, which are assembled together by a distal hub 60 and a proximal base 62.

In the illustrated embodiment, an expandable structure 72 comprising a balloon is located within the basket 56. The balloon structure 72 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material.

The balloon structure 72 presents a normally, generally collapsed condition, as FIG. 2 shows. In this condition, the basket 56 is also normally collapsed about the balloon structure 72, presenting a low profile for deployment into the esophagus 10.

The catheter tube 30 includes an interior lumen, which communicates with the interior of the balloon structure 72. A fitting 76 (e.g., a syringe-activated check valve) is carried by the handle 28. The fitting 76 communicates with the lumen. The fitting 76 couples the lumen to a syringe 78 (see FIG. 3). The syringe 78 injects fluid under pressure through the lumen into the balloon structure 72, causing its expansion.

Expansion of the balloon structure 72 urges the basket 56 to open and expand (see FIG. 3). The force exerted by the balloon structure 72, when expanded, is sufficient to exert an opening force upon the tissue surrounding the basket 56.

Each spine 58 carries an electrode 66 (see FIG. 4). In the illustrated embodiment, each electrode 66 is carried within the tubular spine 58 for sliding movement. Each electrode 66 slides from a retracted position, withdrawn in the spine 58 (shown in FIG. 3) and an extended position, extending outward from the spine 58 (see FIG. 4) through a hole in the spine 58. A push-pull lever 68 on the handle 28 is coupled by one or more interior wires to the sliding electrodes 66. The lever 68 controls movement electrodes between the retracted position (by pulling rearward on the lever 68) and the extended position (by pushing forward on the lever 68). The electrodes 66 have sufficient distal sharpness and strength, when extended, to penetrate a desired depth into tissue the smooth muscle of the esophageal or cardia 20 wall. The desired depth can range from about 4 mm to about 5 mm.

In this arrangement (see FIG. 1), the system 10 includes a generator 38 to supply the treatment energy to the electrodes 66. In the illustrated embodiment, the generator 38 supplies radio frequency energy, e.g., having a frequency in the range of about 400 kHz to about 10 mHz. Of course, other forms of energy can be applied, e.g., coherent or incoherent light; heated or cooled fluid; resistive heating; microwave; ultrasound; a tissue ablation fluid; or cryogenic fluid.

A cable 40 extending from the proximal end of the handle 28 terminates with an electrical connector 42. The cable 40 is electrically coupled to the operative element 12, e.g., by wires that extend through the interior of the handle 28 and catheter tube 30. The connector 42 plugs into the generator 38, to convey the generated energy to the operative element 12.

The electrodes 66 are formed of material that conducts radio frequency energy, e.g., nickel titanium, stainless steel, e.g., 304 stainless steel, or a combination of nickel titanium and stainless steel.

Figure 5:
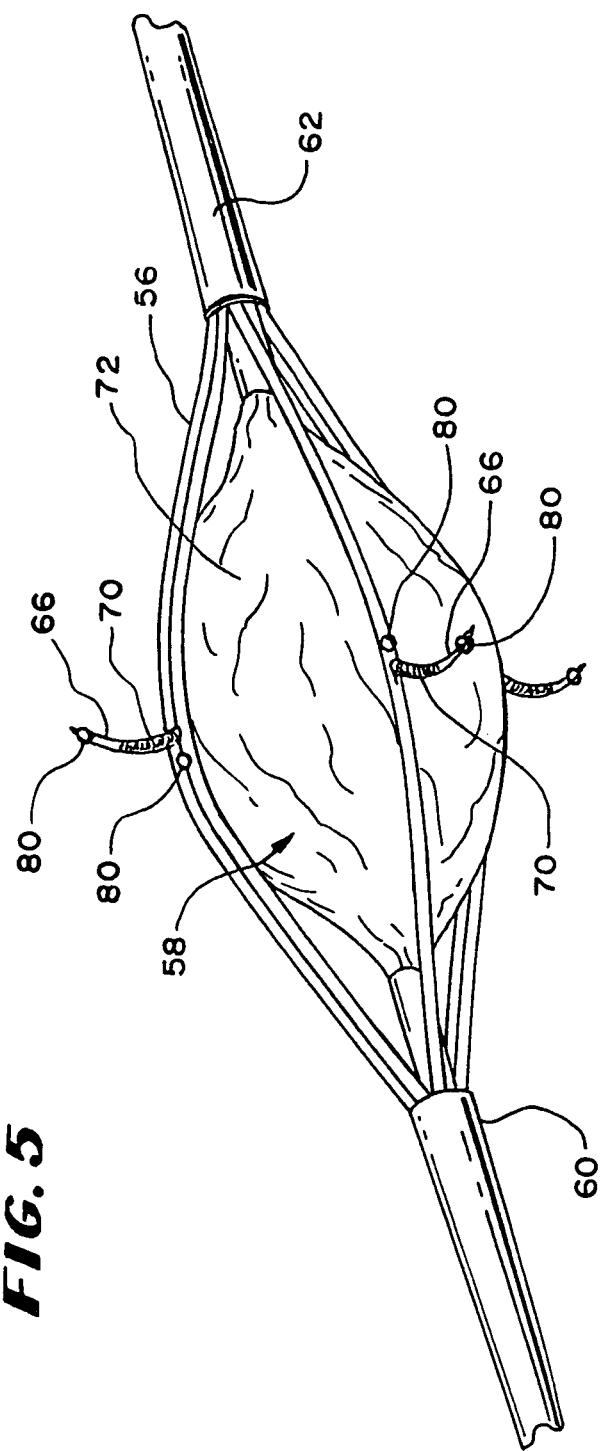
FIG. 5 is an enlarged view of the operative element shown in FIG. 4, with the electrodes extended for use.

In the illustrated embodiment (see FIG. 5), an electrical insulating material 70 is coated about the proximal end of each electrode 66. When the distal end of the electrode 66 penetrating the smooth muscle of the esophageal sphincter 18 or cardia 20 transmits radio frequency energy, the material 70 insulates the mucosal surface of the esophagus 10 or cardia 20 from direct exposure to the radio frequency energy. Thermal damage to the mucosal surface is thereby avoided. The mucosal surface can also be actively cooled during application of radio frequency energy, to further protect the mucosal surface from thermal damage.

In the illustrated embodiment (see FIG. 5), at least one temperature sensor 80 is associated with each electrode. One temperature sensor 80 senses temperature conditions near the exposed distal end of the electrode 66, a second temperature sensor 80 is located on the corresponding spine 58, which rests against the muscosal surface when the balloon structure 72 is inflated.

The system 10 (see FIG. 1) can also include certain auxiliary processing equipment, e.g., an external fluid delivery apparatus 44 for supplying cooling liquid to the targeted tissue, e.g., through holes in the spines, and an external aspirating apparatus 46 for conveying liquid from the targeted tissue site, e.g., through other holes in the spine or elsewhere on the basket 56.

The system 10 also includes a controller 52. The controller 52, which preferably includes a central processing unit (CPU), is linked to the generator 38, the fluid delivery apparatus 44, and the aspirating apparatus 46. Alternatively, the aspirating apparatus 46 can comprise a conventional vacuum source typically present in a physician's suite, which operates continuously, independent of the controller 52. The controller 52 governs the delivery of processing fluid and, if desired, the removal of aspirated material.

The controller 52 also governs the power levels, cycles, and duration that the radio frequency energy is distributed to the electrodes 66, to achieve and maintain power levels appropriate to achieve the desired treatment objectives. The controller 52 can condition the electrodes 66 to operate in a monopolar mode. In this mode, each electrode 66 serves as a transmitter of energy, and an indifferent patch electrode (not shown) serves as a common return for all electrodes 66. Alternatively, the controller 52 can condition the electrodes 66 to operate in a bipolar mode. In this mode, one of the electrodes comprises the transmitter and another electrode comprises the return for the transmitted energy. The bipolar electrode pairs can electrodes 66 on adjacent spines, or electrodes 66 spaced more widely apart on different spines.

The controller 52 includes an input/output (I/O) device 54. The I/O device 54 allows the physician to input control and processing variables, to enable the controller to generate appropriate command signals. The I/O device 54 also receives real time processing feedback information from the temperature sensors 80, for processing by the controller 52, e.g., to govern the application of energy and the delivery of processing fluid. The I/O device 54 also includes a graphical user interface (GUI), to graphically present processing information to the physician for viewing or analysis.

B. Monitoring and Control of Reuse

The handle 28 and the catheter tube 30 form an integrated construction intended for a single use and subsequent disposal as a unit. Alternatively, the handle 28 can comprise a nondisposable component intended for multiple uses. In this arrangement, the catheter tube 30, and components carried at the end of the catheter tube 30 comprise a disposable assembly, which the physician releasably connects to the handle 28 at time of use and disconnects and discards after use. The catheter tube 30 can, for example, include a male plug connector that couples to a female plug receptacle on the handle 28.

To protect patients from the potential adverse consequences occasioned by multiple use, which include disease transmission, or material stress and instability, or decreased or unpredictable performance, the controller 54 includes a module 48 that monitors incidence of use of the device and prevents multiple use.

The module and its interaction with the device 26 can take various forms.

1. Magnetic Core Memory

Figure 6:
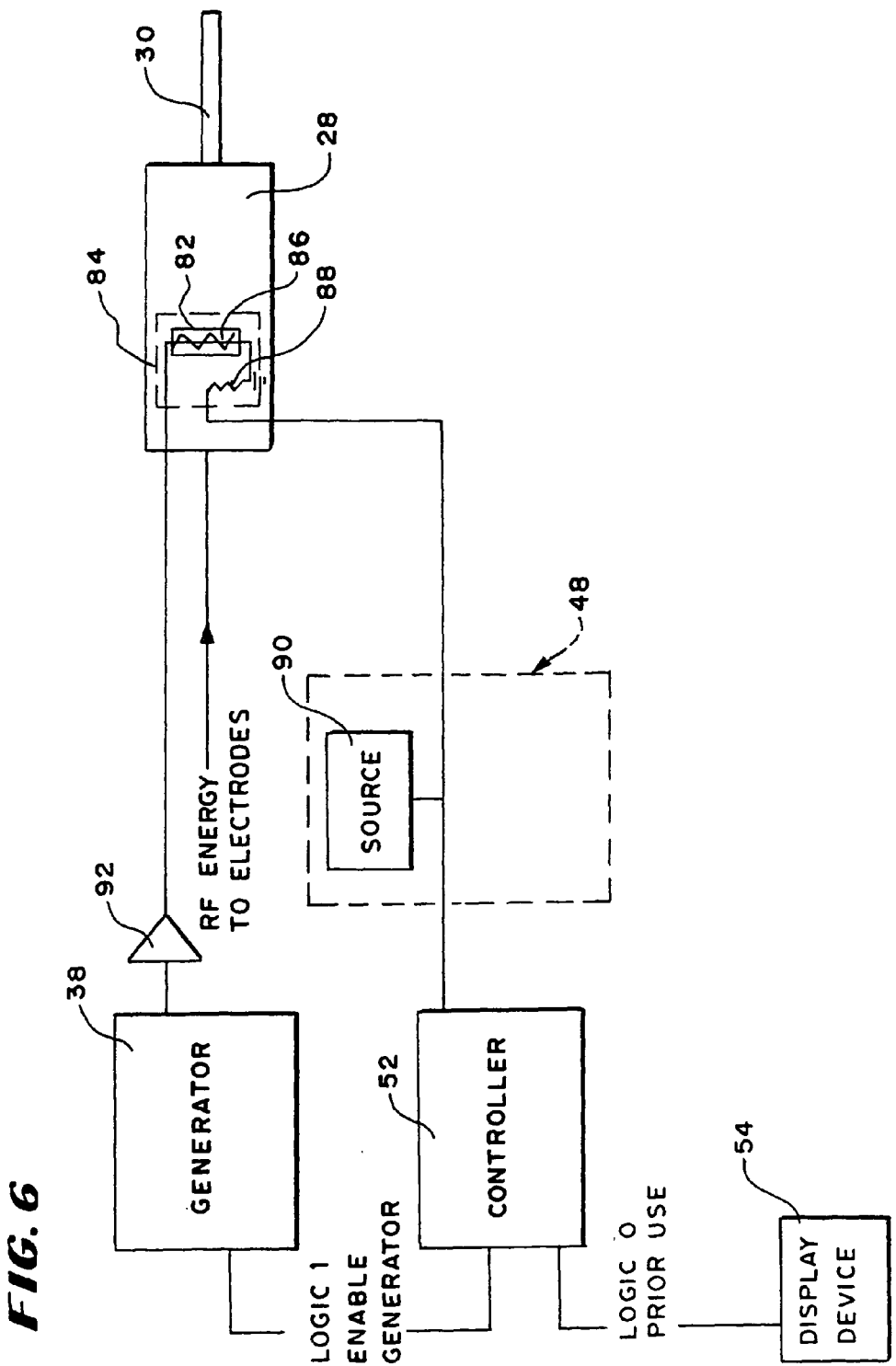
FIG. 6 is a schematic view of a module that uses magnetic core memory to monitor and control incidence of use of the device shown in FIG. 2.

In one embodiment (see FIG. 6), the device 26 carries within its handle 28 a magnetic core 82 comprising, e.g., a toroidal-shaped piece of ferrite magnetic material. Magnetic flux in one direction about the core 82 represents a logic one state and magnetic flux in another direction about the core 82 represents a logic zero state. The core 82, when initially installed in the device 26, possesses a logic one state. The logic one state therefore indicates the absence of prior use of the device 26.

Whenever a device 26 is coupled to the generator 38, the controller 52 operates the module 48 to sense the state of the core 82 prior to enabling the conveyance of radio frequency energy to the electrodes 66. In the illustrated embodiment, the module 48 includes a transformer 84 comprising a primary winding 86, which passes through the core 82, and a secondary winding 88, which is located outside the core 82.

The transformer 84 is coupled to a current source 90. The module 48, when activated, passes current through the primary winding 86 in a direction that will set the core 82 to a logic zero state. If the core 82 initially contained a logic one state, a pulse of voltage occurs at the terminals of the secondary winding 88. The determination of whether the core 82 memory was set at a logic one state or logic zero state prior to sampling by the module 48 is therefore indicated, respectively, by the presence or absence of a pulse in the secondary winding 88.

The controller 52 is coupled to the module 48. When a device 26 is coupled to the generator 38, the controller 52 causes current to flow from the source through the primary winding 86 to set the core 82 to logic zero state. The controller 52 senses the presence or absence of a voltage pulse in the secondary winding 88. In the presence of a sensed voltage pulse; the controller 52 enables the conveyance of radio frequency energy to the device 26.

After a specified time period of use (e.g., at the end of a treatment cycle or after a prescribed time out period), the controller 52 causes current to flow from the generator 38 through an amplifier 92 to the core 82 in the direction that assures that the core 82 retains the logic zero state. The logic zero state of the core 82 therefore indicates that the device 26 has been used.

Should a device 26 having the core 82 set at the logic zero state be again coupled to the generator 38, operation of module 48 to cause current to pass from the source 90 through the primary winding 86 will this time result in the absence of a sensed pulse in the secondary winding 88 (because the core 82 is already set at logic zero state). This condition identifies a device 26 that has been previously been used.

In the absence of a sensed pulse, the controller 52 does not permit radio frequency energy to be conveyed to the device 26. The controller 52 can also generate an output to the display device 54, that results in a visual or audible alarm, informing the operator that the device 26 has been previously used and cannot be used again. The controller 52 also causes current to flow from the generator 38 through the amplifier to the core 82 in the direction that assures that the core 82 of the device 26 remains in a logic zero state.

2. Latching Relay

Figure 7:
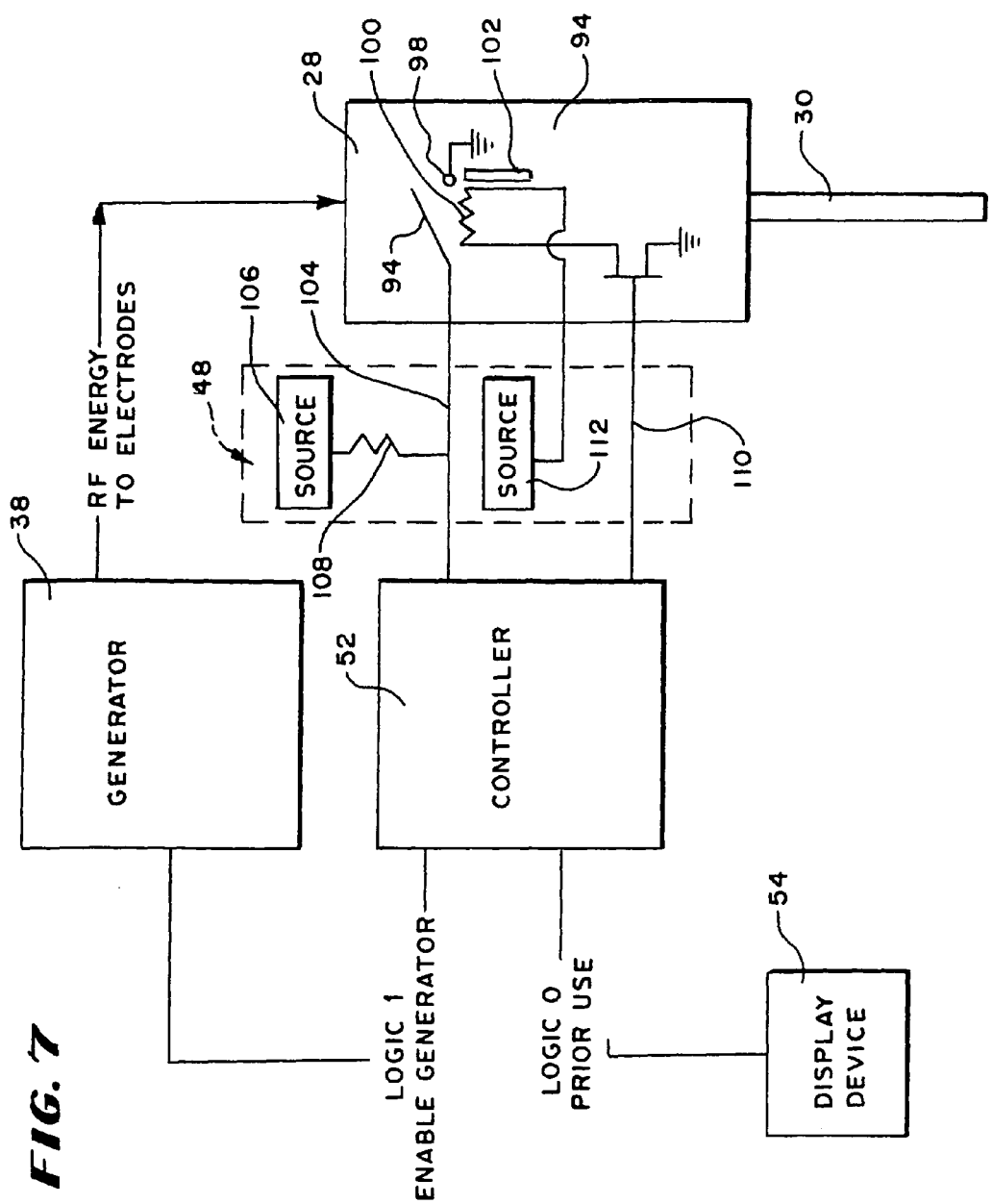
FIG. 7 is a schematic view of a module that uses a latching relay to monitor and control incidence of use of the device shown in FIG. 2.

In another embodiment (see FIG. 7), the device 26 carries within its handle 28 a latching relay 94. The latching relay 94 includes a switch arm 96 and a contact 98 coupled to ground. The switch arm 96 is biased toward an electrically open condition, away from the contact 98. The switch arm 96 can be moved into an electrically closed condition, against the contact 98.

In the illustrated embodiment, the latching relay 94 also includes a coil 100. When energized, the coil 100 moves the switch arm 96 to the electrically closed condition. The latching relay 94 further includes a permanent magnet 102 that, once the switch arm 96 is moved into the electrically closed condition, retains the switch arm 96 in the electrically closed condition.

When initially installed in the device 26, the switch arm 96 is located in the electrically open condition. This is treated as a logic one state. The logic one state indicates that the device 26 has not been used.

Whenever a device 26 is coupled to the generator 38, the controller 52 operates the module 48 to sense the position of the switch arm 96 prior to enabling the conveyance of radio frequency energy to the electrodes 66.

In the illustrated embodiment, the module 48 includes a first circuit 104 that applies current from a source 106 through a resistor 108 to the switch arm 96. The presence or absence of current flow depends whether the switch arm 96 is in the electrically open condition (i.e., the logic one state) or in the electrically closed condition (which is treated as a logic zero state).

The module 48 also includes a second circuit 110 that applies current from a source 112 the coil 100. The application of this current moves the switch arm 96 to the electrically closed condition, which the permanent magnet 102 maintains.

The controller 52 is coupled to the module 48. When a device 26 is coupled to the generator 38, the controller 52 senses the presence of current flow through the first circuit 104. The absence current flow in the first circuit 104 (i.e., the logic one state) indicates that the switch arm 96 is in the electrically open condition. This condition identifies a device 26 that has not been previously used. The controller 52 thereby enables the conveyance of radio frequency energy from the generator 38 to the device 26.

After a specified time period of use (e.g., at the end of a treatment cycle or after a prescribed time out period), the controller 52 also causes current to flow in the second circuit 110. This current moves the switch arm 96 to the electrically closed condition, which is the logic zero state, to indicate that the device 26 has been used.

In the illustrated embodiment, the controller 52 then resamples the current flow through the first circuit 104, to confirm that the switch arm 96 has been successfully moved to the electrically closed condition. If, after current flow through the second circuit 110, no current flow is sensed in the first circuit 104 (indicating that the switch arm 96 is still in the electrically open condition), the controller 52 generates an error signal.

Should a device 26 having the switch arm 96 set at the logic zero state be again coupled to the generator 38, the controller 52 will sense the presence of current flow in the first circuit 104. This indicates prior use of the device 26. In the presence of a current flow in the first circuit 104, the controller 52 does not permit radio frequency energy to be conveyed to the device 26. The controller 52 can also generate an output to the display device 54 that results in a visual or audible alarm, informing the operator that the device 26 has been previously used and cannot be used again.

3. Use Register

Figure 8:
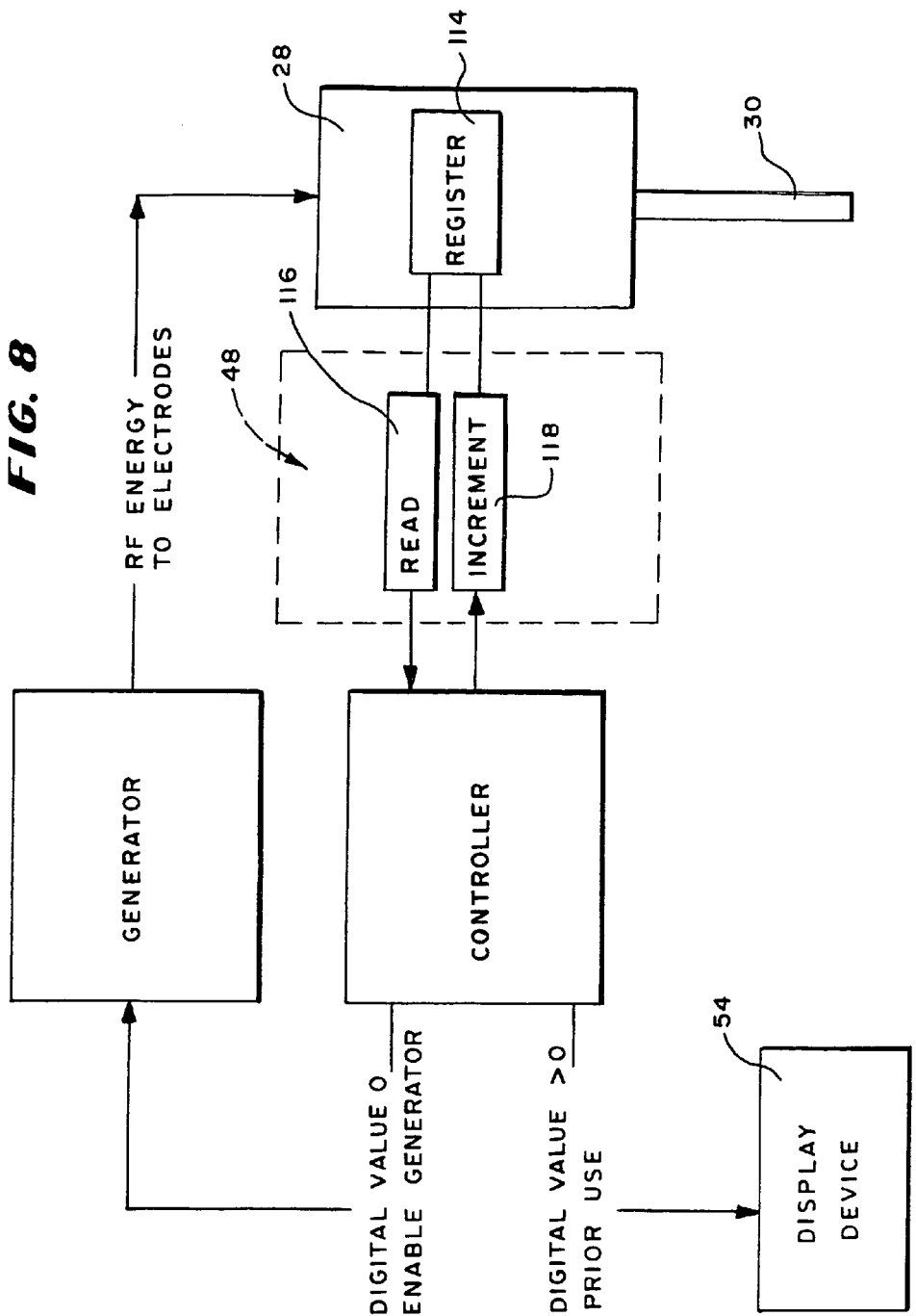
FIG. 8 is a schematic view of a module that uses a microchip register to monitor and control incidence of use of the device shown in FIG. 2.

In another embodiment (see FIG. 8), the device 26 carries within its handle 28 a use register 144. The use register 114 contains a digital value that changes upon use of the device 26.

The use register 114 can comprise a solid state micro-chip, ROM, EEROM, EPROM, or non volatile RAM carried within the handle 28. The use register 114 is initially programmed by the manufacturer of the device 26, e.g., with a digital value of zero. The use register 114 includes an output 116 that generates this digital value upon prompting. The use register 114 also includes an input 118 which increments the digital value upon use of the device 26 to apply radio frequency energy.

Whenever a device 26 is coupled to the generator 38, prior to enabling the conveyance of radio frequency energy to the electrodes 66, the controller 52 operates a module 48 to prompt the use register 114 to output the then resident digital value.

The controller 52 compares the digital value output to a set value indicating no prior use, i.e., a zero value. A resident value of zero identifies a device 26 that has not be previously used. The controller 52 thereby enables the conveyance of radio frequency energy from the generator 38 to the device 26.

After a specified time period of use (e.g., at the end of a treatment cycle or after a prescribed time out period), the controller 52 also generates an input to the use register 114, which increments the resident value to a value above zero, to indicate that the device 26 has been used.

Should a device 26 with a use register 114 having a resident value greater than zero be again coupled to the generator 38, the controller 52 will sense the incremented digital value. This indicates prior use of the device 26. In the presence of an incremented resident value greater than zero, the controller 52 does not permit radio frequency energy to be conveyed to the device 26. The controller 52 can also generate an output to the display device 54 that results in a visual or audible alarm, informing the operator that the device 26 has been previously used and cannot be used again.

The use register 114 can take other forms and retain a more detailed history of use. For example, the use register 114 can be configured to retain a value reflecting the actual period of time during which energy has been applied to the device 26. For example, the use register 114 can comprise an array of magnetic cores, which are embedded by the controller 54 with a pattern of magnetic states that, together, express in binary terms the time-of-use. In this arrangement, the module 48 includes sense amplifiers to determine the magnetic states of the array and, from that, derive the time-of-use history. Alternatively, the use register 114 can comprise a material, e.g., relatively high coercive square loop material, which can be incrementally saturated by pulses of magnetism by the controller 54 over time, such that the magnitude of the charge bears a linear relationship with time-of-use. In this arrangement, the module 48 includes a sense amplifier to determine the magnitude of the charge and, from that, the time-of-use history.

As another example, the use register 114 can comprise a handle-resident magnetic strip. One or more analog magnetic recording heads can be used to record information on the strip during use. The module 48 can comprise a bar-code reader, that reads the code in conventional fashion, e.g., as the user swipes the strip on the handle across the reader. Alternatively, the same heads in the handle can also be employed to read information from the strip for processing by the module 48.

As yet another example, the use register 114 can comprise a miniature stepper or DC motor carried in the handle. The stepper motor operates as the device 26 is used, e.g., to incrementally advance an arm in succession across an array of electrical contacts. The stepper motor advances the arm serially from one contact to another in proportion to the length of time the device 26 is in use. The alignment between the arm and a particular electrical contact is electrically sensed by the module 48, from which the time-of-use can be ascertained.

As yet another embodiment, the use register 114 can comprise a conventional RFID tag element carried within the handle. In this arrangement, the module 48 includes an RFID transponder. The user scans the tag element with the transponder before use, to ascertain time-of-use information, and then scans the tag element with the transponder after use to update the time-of-use information.

In these embodiments, the controller 54 can ascertain whether the time period of previous use or uses retained by the use register 114 is less than a prescribed maximum time period, e.g., 45 minutes. If so, the controller 54 enables operation of the generator 38 in association with the device 26, but only for the time period remaining. If the controller 54 ascertains that the time period of previous use or uses equals or exceeds the prescribed maximum time period, the controller 54 does not enable use of the generator 38.

4. Device Identification Code

In another embodiment (see FIG. 9), the device 26 carries within its handle 28 an element 200 that holds a value that constitutes a unique identification code 214 capable of being read by the module 48 and registered by the controller 54. The identification code 214 is created to be unique to each device 26. That is, each device 26 contains its own unique identification code 214. No two devices 26 share the same identification code 214. The unique identification code 214 can comprise, e.g., a serial number uniquely assigned to the particular device 26, or any other unique code that is not repeated for any other device 26. The code 214 itself can comprise letters, numbers, or combinations thereof.

Figure 9:
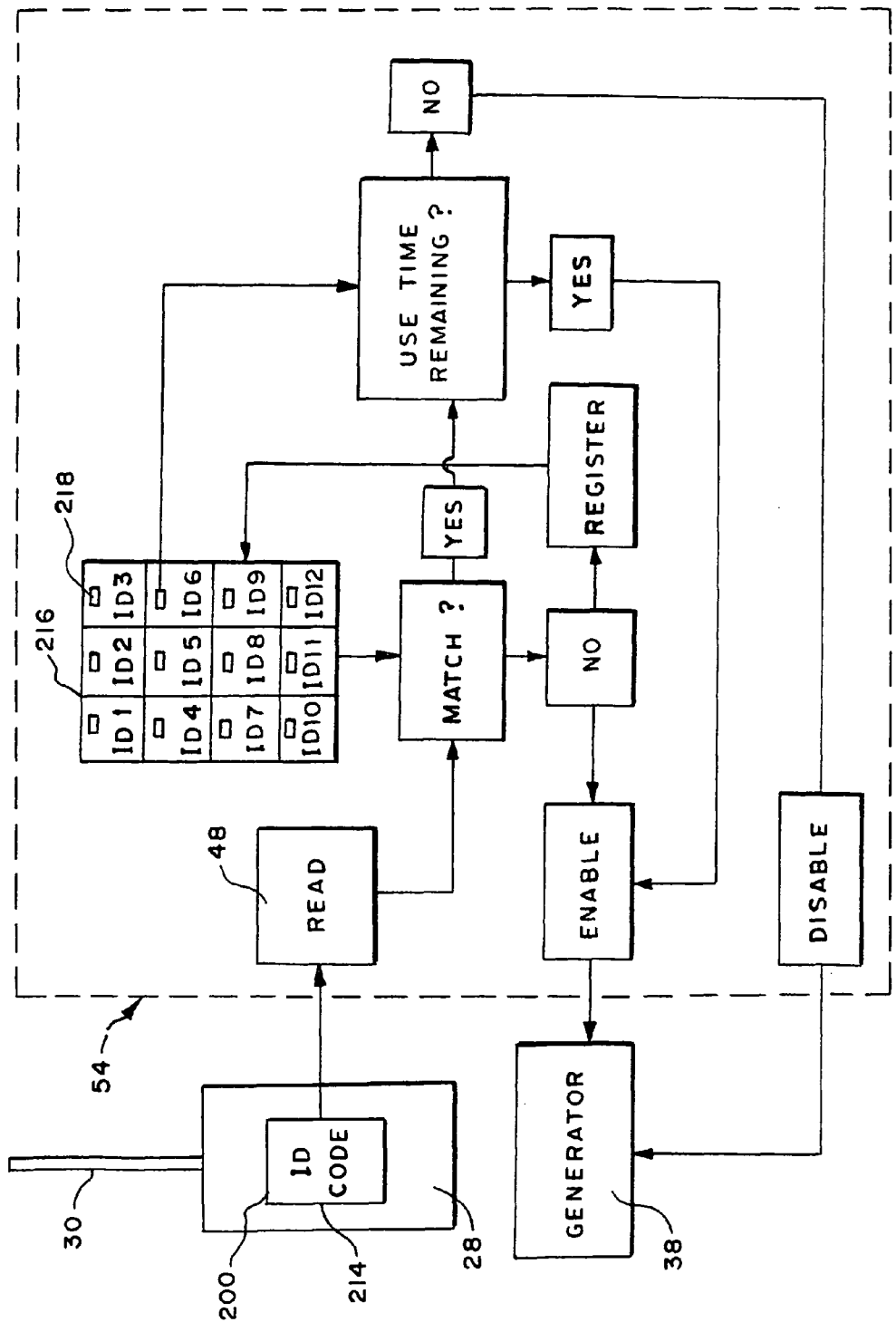
FIG. 9 is a schematic view of a module that uses an identification code to monitor and control incidence of use of the device shown in FIG. 2.

As FIG. 9 shows, when the device 26 is coupled to the controller 54, the module 48 reads the identification code 214 for input to the controller 54. This identification code will be called the "instant identification code."

Following pre-programmed rules, the controller 54 constructs and maintains in non-volatile memory a use table 216. The use table 216 contains all prior identification codes that meet the criteria to be registered by the controller 54. These identification codes will be called the "registered identification codes."

Following pre-programmed rules, the controller 54 compares the instant identification code 214 to all registered identification codes contained in the table 216. In the absence of a match between the instant identification code and any registered identification code, the controller 54 updates the table, i.e., the controller registers the instant identification code by adding it to the table 216. Upon registering the usage key card 202, the controller 54 also enables use of generator 38 in association with the device.

The presence of a match between the instant identification code and any registered identification code indicates a prior use of the device 26. In this circumstance, the controller 54 does not add the duplicative identification code to the table 216 and does not enable use of the generator 38 in association with any device 26. Preferably, the controller 54 outputs to the display device 54 a visual or audible alarm providing notice of prior use.

The element 200 can take various forms. For example, the element 200 can comprise an array of magnetic cores, which are embedded with a pattern of magnetic states that, together, express a multiple bit binary value expressing the identification code. In this arrangement, the module 48 includes sense amplifiers to determine the magnetic states of the array and, from that, derive the binary value.

As another example, the element 200 can comprise a strip containing a magnetic or optical bar code that expresses the identification code. In this arrangement, the module 48 comprises a bar-code reader, that reads the code in conventional fashion, e.g., as the user swipes the strip on the handle across the reader. Alternatively, the identification code can be expressed by conventional RFID tag element carried within the handle. In this arrangement, the module 48 includes an RFID transponder, which scans the tag element to read the code.

The binary bits of the identification code can also be expressed by Hall effect. In this arrangement, the module 48 can comprise either an array of Hall effect sensors, which read the multiple-bit identification code in parallel, or by a single, mechanically movable Hall effect sensor, which reads and processes the code bit-by-bit in a serial swiping motion.

Alternatively, the element 200 can generate the identification code can be expressed in a binary fashion using an array of fiber optics, each fiber expressing a bit of the code. In this arrangement, the module 48 can comprise an array of photo diodes, which read the multiple-bit optical code in parallel, or by a single, mechanically movable photo diode, which reads and processes the optical code bit-by-bit in a serial swiping motion.

The controller 54 can also maintain for each registered identification code in the table 216 a time record 218. The time record 218 contains a value reflecting the period of time during which energy was applied by the generator 38 during the previous permitted use. In this embodiment, when a match occurs between the instant identification code and a registered identification code, the controller 54 ascertains whether the time period of previous use contained in the record 218 is less than a prescribed maximum time period, e.g., 45 minutes. If so, the controller 54 enables a subsequent operation of the generator 38 in association with the device 26, but only for the time period remaining. The controller 54 updates the time record 218 as further use occurs. The controller 54 preferably outputs to the display device the time period of permitted use remaining.

If the controller 54 ascertains that the time period of previous use equals or exceeds the prescribed maximum time period, the controller 54 does not enable use of the generator 38. Preferably, the controller 54 outputs to the display device notice of prior use.

Each embodiment of the module 48, as above described, assures that the device 26, once used, cannot be used a second time. The device 26, when supplied to a customer, can also be accompanied by a floppy disk. The disk, when read by a disk drive associated with the controller 52, identifies the type of catheter in terms of its operational characteristics, the inclusion of temperature sensing, and reuse criteria (e.g., no reuse after a single use, or multiple uses permitted up a prescribed maximum number of uses, or multiple uses permitted up to a maximum time period of use, or multiple uses permitted up to a maximum application of RF energy). The disk can also condition the graphical user interface to display the desired images and data formats, which change depending upon the treatment procedure using the device (e.g., treatment of GERD, fecal incontinence, or urinary incontinence).

Various features of the invention are set forth in the following claims.

We claim:

1. A system for treating a tissue region comprising
a controller, and
a device including a handle, an element within the handle holding a unique identification code, and a use register that senses prior use of the device and senses time-of-use of the device and inputs the time-of-use to the controller, the use register containing a digital value that changes upon use of the device, the use register including an output that generates the digital value upon prompting and an input which increments the digital value upon a period of use of the device to apply radio frequency energy, the use register further retaining a value reflecting an actual period of time during which energy is applied to the device;
the controller including a processing function for processing the time-of-use to enable operation of the device if the time-of-use is less than a prescribed maximum of time period and to disable operation of the device if the time-of-use equals or exceeds the prescribed maximum time period;
the controller registering the unique identification code when the device is coupled to a controller, the controller further maintaining a use table containing prior identification codes that meet a criteria to be registered by the controller, the controller comparing the unique identification code of the device coupled thereto to the prior identification codes to detect an absence or a presence of a match, in the absence of the match the controller updates the use table by adding the unique identification code to the use table and enables use of a generator associated with the device, and in the presence of the match the controller does not add the unique identification code to the use table.

2. A system as in claim 1 wherein the use register comprises an array of magnetic cores.

3. A system as in claim 1 wherein the use register comprises a magnetic strip.

4. A system as in claim 1 wherein the use register comprises a stepper motor.

5. A system as in claim 1 wherein the use register comprises a RFID tag element.

6. The system of claim 1, wherein the controller outputs to a display device notice of prior use of the device.

7. The system of claim 1, wherein in the presence of the match the controller does not enable use of the generator associated with the device.

8. The system of claim 1, wherein the controller updates the time record as fluffier use occurs.

9. The system of claim 8, wherein the controller outputs to a display device notice of prior use.

\* \* \* \* \*